(12) United States Patent
Cloutier et al.

(10) Patent No.: US 7,861,540 B2
(45) Date of Patent: Jan. 4, 2011

(54) AUTOMATED STORAGE AND RETRIEVAL SYSTEM FOR STORING BIOLOGICAL OR CHEMICAL SAMPLES AT ULTRA-LOW TEMPERATURES

(75) Inventors: Robert P. Cloutier, Lancaster, MA (US); Julian Warhurst, Hudson, NH (US); Behrouz Zandi, Lexington, MA (US); James O'Toole, Franklin, MA (US); Halvard Solberg, Merrimack, NH (US)

(73) Assignee: Hamilton Storage Technologies, Inc., Hopkinton, MA (US)

( * ) Notice: Subject to any disclaimer, the term of this patent is extended or adjusted under 35 U.S.C. 154(b) by 518 days.

(21) Appl. No.: 12/020,246

(22) Filed: Jan. 25, 2008

(65) Prior Publication Data

US 2009/0188272 A1 Jul. 30, 2009

(51) Int. Cl.
*F25D 13/06* (2006.01)
*F25D 25/02* (2006.01)

(52) U.S. Cl. .......................................... 62/63; 62/381
(58) Field of Classification Search .................. 62/265, 62/337, 378, 381; 414/273, 806
See application file for complete search history.

(56) References Cited

U.S. PATENT DOCUMENTS

| | | | |
|---|---|---|---|
| 5,735,587 | A | 4/1998 | Malin et al. |
| 6,129,428 | A | 10/2000 | Helwig et al. |
| 6,397,620 | B1 | 6/2002 | Kelly et al. |
| 6,467,285 | B2 | 10/2002 | Felder et al. |
| 6,478,524 | B1 | 11/2002 | Malin |
| 6,536,859 | B1 | 3/2003 | Bathe |
| 6,568,770 | B2 | 5/2003 | Gonska et al. |
| 6,581,395 | B2 | 6/2003 | Felder et al. |
| 6,688,123 | B2 | 2/2004 | Felder et al. |
| 6,718,776 | B2 | 4/2004 | Wessling et al. |

(Continued)

FOREIGN PATENT DOCUMENTS

EP 0725133 B1 12/1998

(Continued)

OTHER PUBLICATIONS www.orientalmotor.com Oriental Motor U.S.A. Corp., pp. 1 and 2, Jan. 22, 2008, Torrance, California.

(Continued)

*Primary Examiner*—Frantz F Jules
*Assistant Examiner*—Emmanuel Duke
(74) *Attorney, Agent, or Firm*—Andrus, Sceales, Starke & Sawall, LLP

(57) ABSTRACT

An automated storage and retrieval system stores containers, typically containing biological or chemical samples, at ultra-low temperatures, i.e., from about −50° C. to about −90° C., preferably about −80° C. under normal operating conditions. Dry gas air flows are used to reduce moisture and the consequential frost within the freezer compartment. A custom insulated door is provided with an access module and a tube picking compartment as well as servo motors for controlling a robot within the ultra-low temperature freezer compartment. The robot automatically places sample storage containers in stationary storage racks within the freezer compartment. Magnetic couplings are used to transmit mechanical power from outside of the freezer compartment to the robot inside of the freezer compartment. The robot has a simplified mechanical configuration. The custom door can be readily attached to standard freezer bodies.

23 Claims, 11 Drawing Sheets

U.S. PATENT DOCUMENTS

| | | |
|---|---|---|
| 6,752,479 B2 | 6/2004 | Ferger et al. |
| 6,941,762 B2 | 9/2005 | Felder et al. |
| 6,990,819 B2 | 1/2006 | Darling |
| 7,013,197 B2 | 3/2006 | Melching et al. |
| 7,013,198 B2 | 3/2006 | Haas |
| 7,059,138 B2 | 6/2006 | Bonaquist et al. |
| 7,214,022 B2 | 5/2007 | Melching |
| 7,227,746 B2 | 6/2007 | Tanaka et al. |
| 7,290,396 B2 | 11/2007 | Rampersad et al. |
| 7,314,341 B2 | 1/2008 | Malin |
| 2002/0198610 A1 | 12/2002 | Malin et al. |
| 2004/0154322 A1 | 8/2004 | Felder et al. |
| 2004/0213651 A1 | 10/2004 | Malin |
| 2004/0258566 A1 | 12/2004 | Smith |
| 2005/0028538 A1 | 2/2005 | Darling |
| 2005/0069401 A1 | 3/2005 | Malin |
| 2006/0053825 A1 | 3/2006 | Owen et al. |
| 2006/0105450 A1 | 5/2006 | Owen |
| 2006/0289371 A1 | 12/2006 | Malin |
| 2007/0064383 A1 | 3/2007 | Tanaka et al. |

FOREIGN PATENT DOCUMENTS

| | | |
|---|---|---|
| EP | 1074488 B1 | 9/2002 |
| EP | 1253817 A2 | 10/2002 |
| EP | 1211197 B1 | 2/2003 |
| EP | 1441026 A1 | 7/2004 |
| EP | 1443101 A1 | 8/2004 |
| EP | 1634496 A1 | 3/2006 |
| EP | 1639892 A1 | 3/2006 |
| EP | 1721964 A1 | 11/2006 |
| EP | 1757883 A2 | 2/2007 |
| EP | 1354028 B1 | 9/2007 |
| EP | 0853657 B1 | 12/2007 |
| EP | 1477813 B1 | 2/2008 |
| JP | 2007010531 | 1/2007 |
| WO | WO 02/059251 A2 | 8/2002 |
| WO | WO 2006/074568 A1 | 7/2006 |
| WO | WO 2006/074569 A1 | 7/2006 |

OTHER PUBLICATIONS http://www.applied-motion.com/products/servo/motors/NMseries.php, Applied Motion Products: Motors, Motion Control Products, Drives and Controls; pp. 1-6, 2006.

ANSI/SBS Jan. 2004, ANSI American National Standards Institute, Society for Biomolecular Sciences for Microplates-Footprint Dimensions, pp. 1-8, 2004.

http://www.airtxinterntional.com/catalog/82000.php, AiRTX Intemational:Air Knives:Aluminum 85000 Series, pp. 1-4. Jan. 22, 2008.

www.honeywell.com/sensing, Honeywell, HIH 4000 Series, pp. 1-8, Minneapolis, Minnesota, Jan. 2007.

http://www.rtslifescience.com/html/compound-magagement.htm, RTS Group—Compound Management, pp. 1-14, 2005.

http://www.nexusbio.com/Products/SampleManagement/compound_storage.php Nexus Biosystems:: Universal Store—Compound Storage System,pp. 1-3, Jan. 15, 2008.

http://www.matrical.com/MatriStore2.php, MatriStore—Compound Storage and Retrieval System, pp. 1-6, Spokane, Washington 2007.

LiCONiC Instruments, Product Overview, pp. 1-2, Woburn, Massachusetts, Jul. 19, 2007.

htto://www.therrno.com/com/dcs/product/detail/1,,10120038,00.html, Automated Sample Library at -90C-Thermo Scientific Product Information, ©2007.

Thermo Electron BioBank -80C Automated Sample Library Management System, Ontario, Canada.

Thermo Scientific BioBank -80C Automated Sample Library Management System.

http://www.tecan.com/pape/content/index.asp?MenuID, Tecan Group Ltd.—News, pp. 1-2, Switzerland, 2008.

REMP Automated Sample Stores, Sample Safe, Mannedorf, Switzerland, 2007.

REMP Storage Systems, Storage Family, Mannedorf, Switzerland, 2007.

AUTOMATED STORAGE AND RETRIEVAL SYSTEM FOR STORING BIOLOGICAL OR CHEMICAL SAMPLES AT ULTRA-LOW TEMPERATURES

FIELD OF THE INVENTION

The invention relates to automated storage and retrieval systems for ultra-low temperature freezers used primarily to store biological or chemical samples.

BACKGROUND OF THE INVENTION

Storage of biological and chemical samples is becoming widespread in the biotechnology and medical industries. To preserve many of these samples, the samples must be stored at or below freezing temperatures. Generally speaking, a regular freezer operates from −5° C. to −20° C., and an ultra-low temperature freezer operates from about −50° C. to about −90° C. (preferably at or about −80° C.) and a cryogenic freezer operates from about −140° C. to −196° C. (the boiling point of liquid nitrogen). The present invention is directed to ultra-low temperature freezers operating in the range of −50° C. to about −90° C., and preferably −80° C.

U.S. Pat. No. 6,941,762 to Felder et al., as well as U.S. Pat. Nos. 6,688,123; 6,581,395; and 6,467,287 also by Felder et al., describe various embodiments of an automated ultra-low temperature storage and retrieval system. In particular, these patents describe a system having a freezer compartment that is maintained at an ultra-low temperature from −50° C. to −90° C., preferably at about −80° C., under normal operating conditions. Storage racks are mounted within the insulated, ultra-low temperature freezer compartment. The storage racks can be mounted either in a fixed position or mounted to a rotating carousel. A mechanical robot is provided within the ultra-low temperature storage compartment to place sample storage containers in the storage racks and retrieve the storage containers from the racks. The sample storage containers are typically SBS footprint compatible, and take the form of microtiter plates, tube storage racks, reservoirs or other SBS format containers. The robot also communicates with an access module in order to introduce the sample storage containers into the system and retrieve the containers for use outside of the system. The Felder et al. patents describe the use of a climate control chamber which uses a dry gas purge to reduce the humidity in the access module. It is typical to locate the drive motors outside of the freezer compartment, not only because the motors have difficulty operating at ultra-low temperatures, but also to reduce heat generation within the ultra-low temperature storage compartment.

These ultra-low temperature storage and retrieval systems have a capacity of several hundred or more sample storage containers, such as microtiter plates or tube storage racks. Although there are a wide variety of manufacturers for freezer systems that are capable of cooling the storage compartment to an ultra-low temperature of, for example −80° C., the cooling process with some freezer systems is not particularly efficient. Normally, it takes about 24 hours to cool the freezer compartment to −80° C. in preparation for loading the system with biological or chemical samples.

It has been found that many biological samples stored in ultra-low temperature systems are often contained in sealed plastic laboratory tubes held in tube storage containers in arrays of, for example, 48 or 96 tubes. In some cases, a two-dimensional barcode is adhered to the bottom of the tubes that is able to be read through the bottom of the storage containers. In other cases, a one-dimensional bar code is placed on the sidewall of the tube. In either case, bar coding facilitates data entry into the control system which keeps track of the location of each of the biological samples. It is also typical for the sample storage containers themselves to have a barcode.

In these ultra-low temperature storage and retrieval systems, it is desirable to reduce the accumulation of frost within the ultra-low temperature freezer compartment. Excessive frost can cause the system, and in particular the robot and the other components of the retrieval mechanism, to malfunction. Therefore, it is necessary to defrost the systems on a fairly regular basis. The defrosting procedure, however, is normally time-consuming. Typically, all of the sample storage containers must be transferred to a separate ultra-low temperature freezer, and then after defrosting and recooling of the system, reintroduced on a one-by-one basis. Not only is the defrosting procedure quite time-consuming, but it can also lead to premature wear of system components, for example, robotic bearings or other components. One object of the present invention is to reduce the amount of moisture ingress allowed into the ultra-low temperature freezer compartment during normal operation, in order to reduce the need to defrost as often as is now typical.

While a significant amount of moisture in current day systems is allowed into the ultra-low temperature freezer compartment through the access module when sample storage containers are introduced or retrieved, moisture and heat can also leak into the insulated, ultra-low temperature freezer compartment at any location where the freezer wall is breached. For example, openings to pass a mechanical drive shaft through the freezer wall even if the opening is sealed can provide an opportunity for leakage, especially after the seal is worn.

To commercially manufacture the system disclosed in Felder et al., a custom designed freezer body was used to house the storage racks and storage carousel, and the robot and its drive mechanism, as well as accommodate the access module and drive motors. Certain components such as the carousel and the racks, as well as supports for the robot, are mounted directly to the inner wall of the freezer compartment. This can lead to distortion problems during installation because of material shrinkage due to the ultra-low temperatures. It should be noted that the placement of the reach arm or interchange mechanism must be accurate, especially with respect to the rotational accuracy, otherwise the system may malfunction and could possibly cause loss of samples. Therefore, it has not been uncommon for technicians to spend significant time and effort accounting for thermal distortions during system set-up.

Also, referring to the system disclosed in Felder et al, the robot is mounted on a cylindrical base which is mounted through the floor of the freezer compartment. The robot motors are mounted to the cylindrical base outside of the freezer compartment. The cylindrical base, as well as substantially the entire robot, are rotated in order to position the reach arm. However, this design requires an active seal between the cylindrical base and the floor of the freezer which can at times be somewhat difficult to achieve and can become a source of wear. In a similar fashion, the motor for driving the storage rack carousel is mounted below the floor of the freezer and its drive shaft must penetrate the wall of the floor of the freezer in order to drive the carousel. Again, although the penetrating drive shaft is sealed, the breaching of the freezer wall provides an opportunity for heat and/or moisture to leak into the ultra-low temperature freezer compartment.

An issue also arises when it is desired to retrieve less than all of the storage tubes from a stored sample container, which is more often the case than not in these applications. It is not desirable to remove the entire container from the system. The removal procedure allows for the ingress of moisture in to the ultra-low temperature storage compartment, and also threatens that the other samples held in the same container will be thawed at least partially when removed from the system even if temporarily. While tube picking mechanisms are generally known in the art, the environment within the ultra-low temperature freezer compartment is typically too cold to ensure reliable operation of conventional tube picking mechanisms.

SUMMARY OF THE INVENTION

The invention is an improved automated storage and retrieval system and method for storing containers at ultra-low temperatures, i.e., from about −50° C. to about −90° C., preferably about −80° C. under normal operating conditions. Typically, the containers will contain biological or chemical samples as is known in the art.

In one aspect of the invention, the system comprises an ultra-low temperature freezer having an insulated body and an insulated door with the ultra-low temperature storage compartment contained therein. The freezer body has a substantially continuous foam insulated wall which, in this aspect of the invention, is not breeched by providing openings for any mechanical drive shafts. A rugged frame structure to which the storage racks and the robot are mounted is set and stabilized inside the insulated, ultra-low temperature freezer compartment. This configuration substantially eliminates the time and effort needed to accommodate thermal distortions during the installation process. The insulated freezer door is mounted to the freezer body, as expected, for example, via hinges and a latch mechanism, and the door is closed during normal operation of the system. Further, in accordance with this aspect of the invention, the access module for introducing storage containers into the ultra-low temperature storage compartment and for retrieving samples is integrated into the insulated freezer door. The samples are taken from the access module in the door via a reach arm on the robot located inside the ultra-low temperature storage compartment. The access module includes a drying chamber, which is preferably held at or near room temperature, in which moisture is purged before providing access into the ultra-low temperature compartment. The robot drive motors are also mounted to the door outside of the ultra-low temperature storage compartment. Preferably, magnetic couplings provide mechanical power from the robot drive motors mounted to the door outside of the ultra-low temperature compartment to the robot drives located inside of the ultra-low temperature compartment. The ultra-low temperature storage and retrieval system can therefore be manufactured using a standard freezer body, without retrofit, with a customized door incorporating the access module and the robot drive motors. Whether the drive motors are mounted on the insulated door or not, the use of magnetic couplings allows power to be transmitted to the robot without breaching the insulated wall of the freezer compartment.

While the transmission of power from the robot drive motors outside of the ultra-low temperature compartment to the robot inside the storage compartment is preferably accomplished with magnetic couplings, the transmission of mechanical power may be accomplished by mechanical transmission means such as a mechanical drive shaft penetrating the inner wall of the insulated freezer door into the ultra-low temperature storage compartment. In this case, the system would still have the advantage of providing the robot drive motors on the customized door.

The preferred robot has a reach arm that is able to move vertically (vertical motion), horizontally (reach motion), and rotate clockwise or counterclockwise in a horizontal plane (rotational motion). In the preferred embodiment, chain drive mechanisms driven by the set of magnetic couplings within the ultra-low temperature freezer compartment drive each of these movements, although other types of drive mechanisms can be used inside the ultra-low temperature storage compartment. The storage rack preferably consists of a plurality of tray columns arranged circumferentially about the rotational axis of a turntable holding the reach arm of the robot except for a small portion of the circumference in which components of the robot are located. With this preferred configuration, there is no need for a motor or any mechanism to rotate the stationary storage racks, and each tray position within the storage racks is accessible by the reach arm on the turntable. Further, there is no need to provide a physical opening for drive shafts through either the walls of the freezer body or the inner wall of the insulated door.

In another aspect of the invention, the access module, whether located on the door or not, includes a dry gas knife which blows a curtain of dry gas over the access opening into the ultra-low temperature compartment when the access door into the compartment is open. Typically, ambient relative humidity will be about 40%-50%. The dry gas curtain, e.g., either dry air or dry nitrogen, begins to flow at 3-5 cubic feet per minute once the access module cover is closed and the system is instructed to either place a sample storage container into the ultra-low temperature storage compartment or retrieve a sample from the compartment. The curtain of dry gas is typically supplied for about 30 seconds into the access module chamber while the access door into the ultra-low temperature storage compartment is closed and the cover is closed. The positive pressure within the cover causes some air to flow from the access module chamber, with the relative humidity within the cover decreasing to about 5%-10% on average after about 30 seconds of purge. Preferably, the relative humidity sensor is used to monitor the relative humidity within the access module chamber, although time-based control can be used as well. When the access door into the ultra-low temperature compartment is opened, the air curtain continues to blow across the opening, preferably from its top edge. It has been found that, absent a dry gas curtain, natural convection through this opening causes cold air to rush out through the bottom of the opening and relatively warm, moist air to rush in through the top of the opening into the ultra-low temperature compartment. The dry gas curtain serves to disturb this natural convection. Also, it is believed that the dry gas curtain tends to be directed somewhat into the ultra-low temperature compartment when the access door is opened, thereby rendering the ingress of air into the ultra-low temperature compartment to be relatively drier.

The system also preferably includes a dry gas bleed system, which includes an electronically controlled dry gas bleed into the ultra-low temperature storage compartment, and a pressure sensor for measuring the pressure within the ultra-low temperature storage compartment. Preferably, a dry gas inlet port is provided on the customer door, as is an outlet port. Solenoid valves control the flow of dry gas into the storage compartment through the dry gas inlet port, as well as flow through the outlet port from the ultra-low temperature compartment. The pressure sensor monitors the pressure within the freezer storage compartment and instructs the system to bleed in dry gas in the event that the pressure within the compartment decreases below atmospheric pressure. Maintaining the pressure within the ultra-low temperature storage compartment at or above atmospheric pressure helps to prevent the ingress of moisture through the seal between the freezer compartment and the freezer door, as well as through any other seals or components which may be subject to leaking, even if minimal. During system start-up, there would normally be a relatively high flow of dry gas into the storage compartment in order to equalize pressure as the system initially cools to −80° C. During normal operation of the freezer, the freezer compressor will cycle on and off, normally between −82° C./−83° C. to −77° C./−78° C., causing the pressure within the storage compartment to rise and fall. During these cycles, the dry gas air flow would normally be at a low flow rate, such as 3 cubic feet per hour in order to equalize the pressure.

The preferred system may also include a tube picking chamber which holds a tube picking mechanism. The tube picking chamber is preferably incorporated into the insulated door. An access shutter is located between the tube picking chamber and the ultra-low temperature storage compartment, and is preferably located such that the reach arm for the robot can supply and retrieve plates from the tube picking mechanism. The access shutter for the tube picking chamber remains closed, isolating the tube picking chamber from the ultra-low temperature storage compartment under normal storage conditions. When access to the tube picking chamber is requested, dry gas is introduced into the tube picking chamber with the access shutter closed in order to reduce the relative humidity within the compartment. A relative humidity sensor is located within the tube picking chamber for this purpose. When the relative humidity has been lowered to the desirable level, for example less than 2% relative humidity, the access shutter is opened and cold air from the ultra-low temperature storage compartment is allowed to flow into the tube picking chamber. A temperature sensor is also located in the tube picking chamber. The access shutter is opened and closed as necessary to maintain the temperature in the tube picking chamber at a freezing temperature that is above the ultra-low temperature in the ultra-low temperature storage compartment, preferably −5° C. to −20° C., e.g. about −20° C. In this manner, the tube picking mechanism, and its mechanical and electrical components, can operate in a less harsh environment which greatly improves reliability. On the other hand, by maintaining the tube picking chamber at a subfreezing temperature, the other samples in tube storage containers that are desired to be retrieved need not exit the system. This not only protects the other samples from premature thaw and harm, but also reduces the risk of moisture flow into the ultra-low temperature compartment. Further, tube storage containers can be shuttled in and out of the tube picking compartment at a relatively fast pace, thus shortening exposure times outside of the −80° C. environment for samples not selected for retrieval.

As mentioned, the storage racks remain stationary within the ultra-low temperature chamber which simplifies the system mechanically. The robot preferably comprises a turntable that supports the reach arm. The turntable has a rotational axis that is parallel to and offset from the vertical lead screw with there being a support structure from the vertical lead screw to the turntable. The robotic mechanism has been simplified so that the vertical lead screw and vertical guide rails for the reach arm do not rotate about the turntable axis. This simplified structure is durable and facilitates accurate positioning of the reach arm without excessive motion of mechanical parts. The most critical degree of motion for precision is the rotational motion of the turntable and reach arm. The turntable is preferably driven by a gear that is coupled to one of the drive motors, and can be rotated in either direction. In order to minimize mechanical backlash and improve positional accuracy, it is preferred that the turntable always be rotated in the same direction just prior to the placement or retrieval of a sample storage container in a storage rack. For example, it may be desirable that the turntable always rotate in the clockwise direction just prior to placement or retrieval. If movement requires counter-clockwise rotation, the system preferably overshoots in the counter-clockwise direction and then returns in the clockwise direction just prior to placement or retrieval.

Other features and aspects of the invention may be apparent to those skilled in the art upon reviewing the following drawings and description thereof.

DETAILED DESCRIPTION OF THE INVENTION

Figure 1:
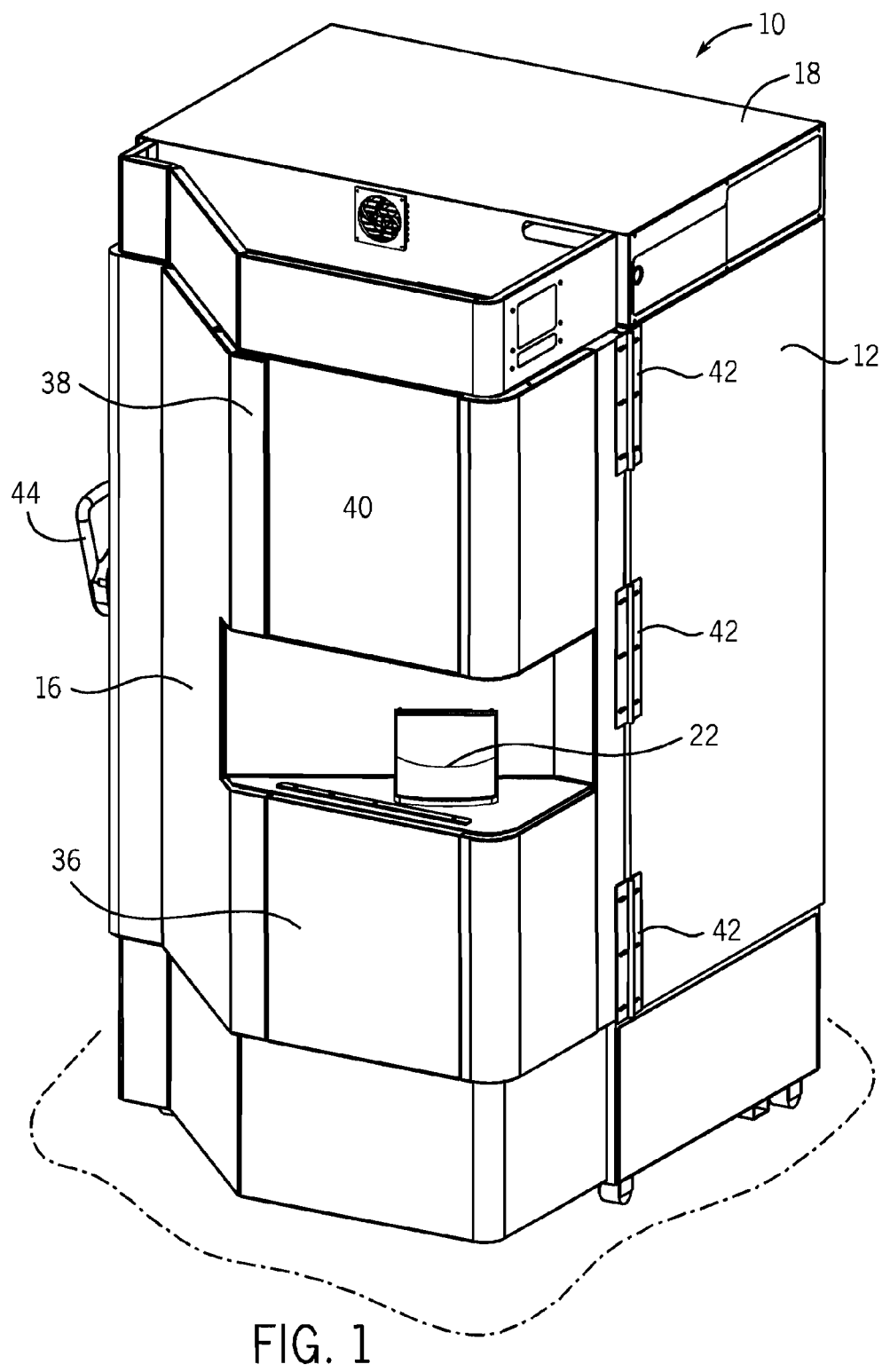
FIG. 1 is a perspective view of an automated storage and retrieval system for storing containers at ultra-low temperatures in accordance with an embodiment of the invention.
Figure 2:
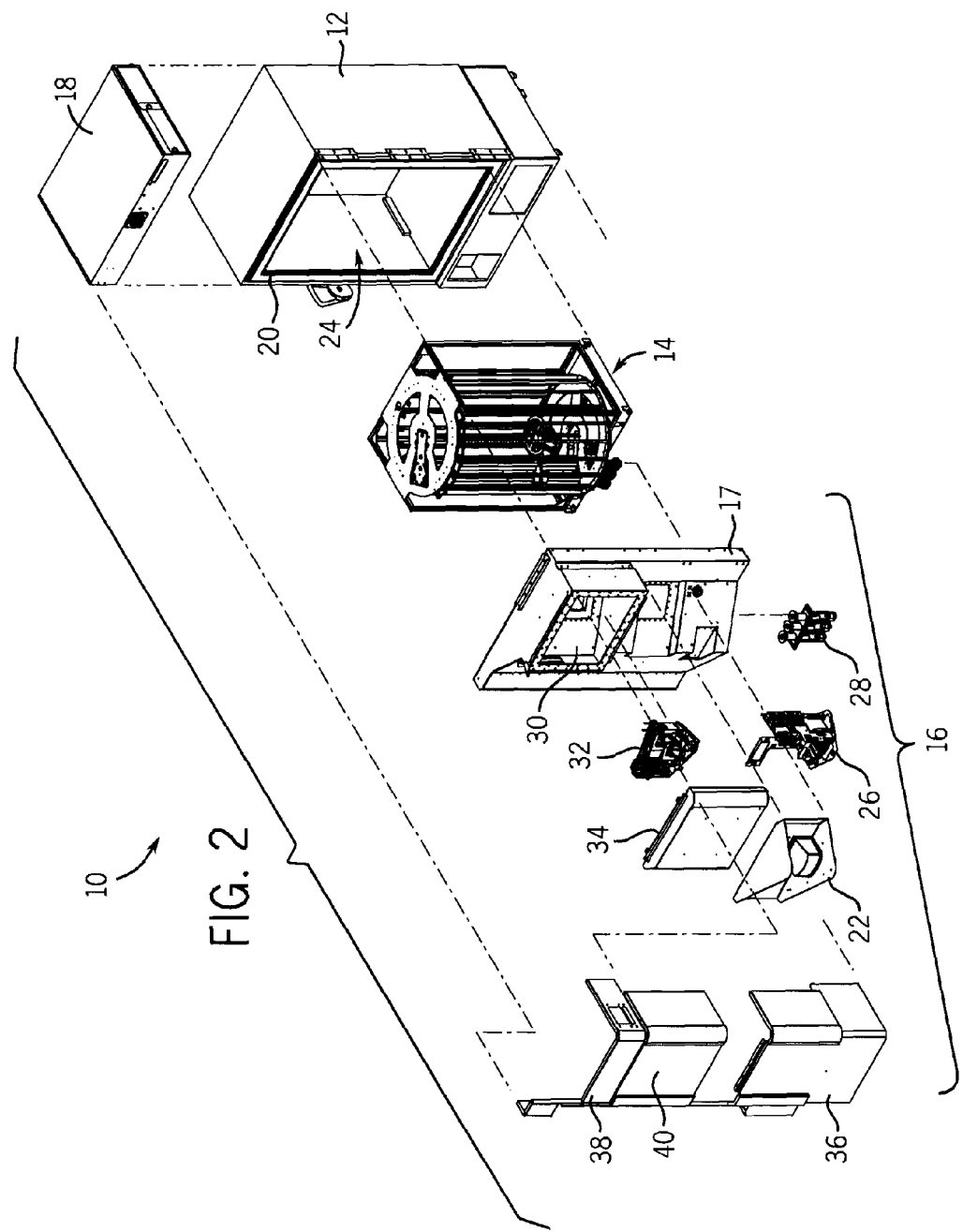
FIG. 2 is an exploded view of the ultra-low temperature, automated storage and retrieval system shown in FIG. 1.

The Figures illustrate various aspects of a preferred embodiment of the invention. Referring to FIGS. 1 and 2, an automated storage and retrieval system 10 is configured to store sample storage containers, such as microtiter plates, racks for holding sealed storage tubes, or reservoirs at ultra-low temperatures. As mentioned, the system 10 is preferably designed to store SBS footprint compatible storage containers. The system 10 generally comprises a freezer body 12 for a standard ultra-low temperature freezer, an internal storage rack and robot assembly 14, a custom insulated door 16, and an electrical box 18. The preferred freezer body 12 is an upright −86° C. freezer body, purchased from Thermo Scientific, the Forma 907 Series, which is designed for ultra-low temperature storage for pharmaceutical, biotech and blood bank applications. These commercially available freezers typically come with installed racks, although these racks are not used in the present invention. In these freezers 12, it is typical, as mentioned, for the freezer compartment 24 to be lined with stainless steel sheets, however, closed cell foam insulation seals the freezer compartment from the ambient environment. The preferred size for the storage compartment 24 ranges from about a 19 cubic feet to a 28 cubic feet capacity. The freezer body 12 includes a double or triple seal 20 along the door opening to reduce heat and moisture ingress into the storage compartment, as is known in the art. While the preferred freezer body 12 is an upright Forma 907 as mentioned, other standard freezers capable of cooling to −80° C. may be suitable as well.

The insulated custom door 16 includes an insulated panel 17 and several other components. The door 16 includes an access module 22 in which sample storage containers are placed in order for transfer into storage racks 46, FIG. 3, in the freezer compartment 24. An electrical control and pneumatic package 26 is also mounted to the insulated door 16 as are servo motors 28 and magnetic couplers for driving the robot 48, FIG. 3. The insulated door 16 also includes a tube picker compartment 30 in which a tube picking apparatus 32 resides. An inside cover 34 having a window is permanently mounted to the outside of the insulated door panel 17 in order to enclose the tube picking chamber 30. Decorative covers 36, 38 are mounted to the front of the insulated door panel 17. The upper decorative cover 38 has a window 40, preferably made of smoked polycarbonate, to allow viewing of the tube picking apparatus 32 through the window on the inside cover 34. The box 18 set on the top of the freezer body 12 preferably houses an electronic controller, power distribution electronics, a battery and also includes an inlet port for a compressed dry gas source (not shown). The preferred dry gas source is from a tank of liquid nitrogen supplied so that the dew point is better than −70° C., although other sources of compressed dry air or dry nitrogen can be used. The insulated front door 16 is mounted to the freezer body using hinges 42, and a latch 44, as is known in the art. Although not shown in FIG. 1, the system 10 would include a monitor and user interface as is known in the art, such as used in connection with the TekCel™ Biological Storage Unit, or the Hamilton Storage Technologies TubeStor™.

Figure 3:
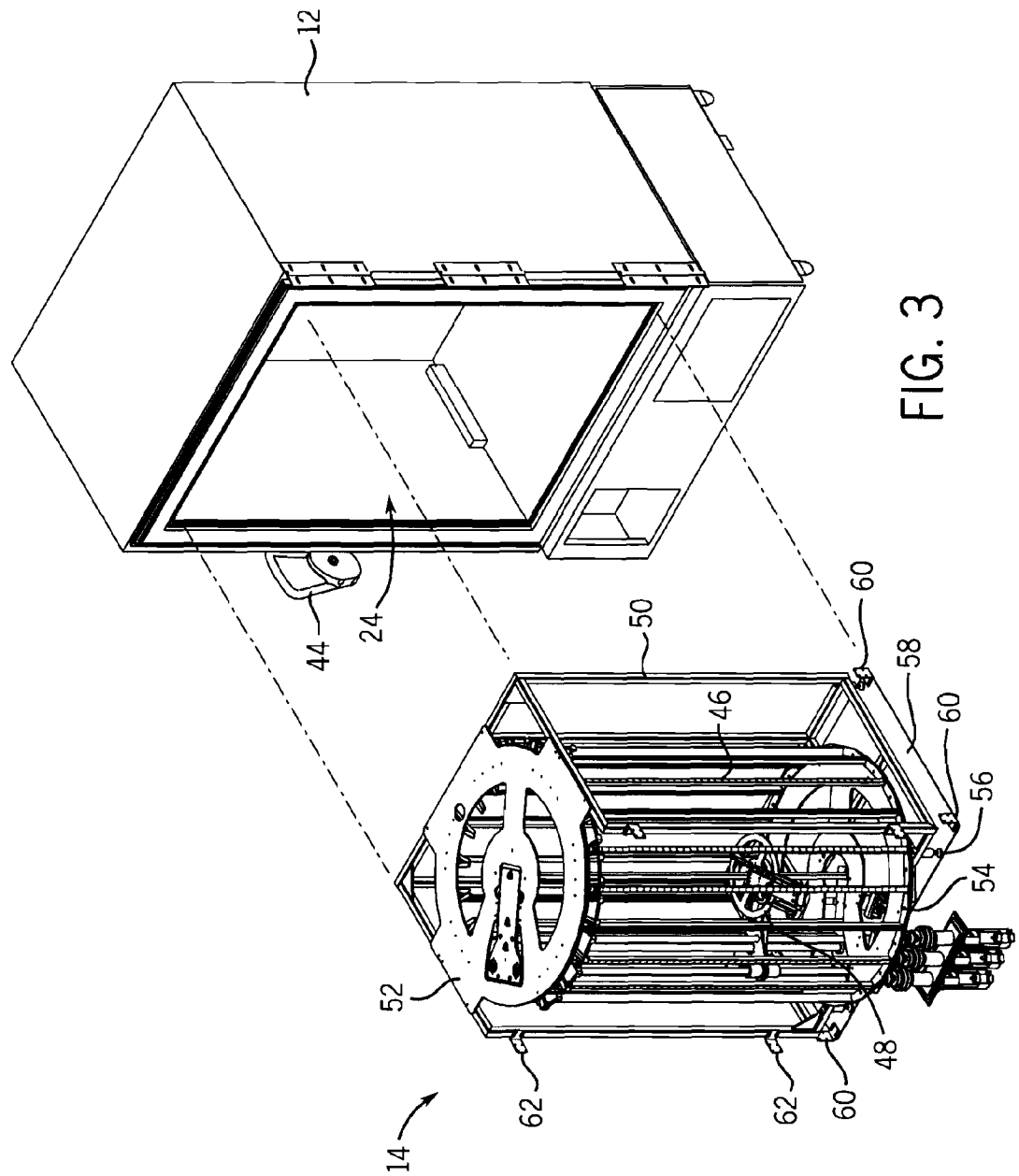
FIG. 3 is a partial exploded view showing primarily the insertion of a frame with a stationary storage rack and a robot mounted thereto into the storage compartment of an ultra-low temperature freezer.

FIGS. 3-7 illustrate the preferred construction of the stationary storage rack 46 and the robot 48, their attachment to a rigid frame 50, and their placement within the freezer compartment 24. In FIG. 3, the frame 50 is made of 1 inch stainless steel tube. A top support plate 52, also made of stainless steel, is attached to the top surface of the frame 50. A lower support plate 54 made of stainless steel is mounted to a lower part of the frame 50. The storage racks 46 are mounted to the support plates 54, 52. The robot 48 is mounted indirectly to the plates 52, 54, as is shown best in FIG. 5. The frame 50 includes adjustable feet 56 that are used to balance the storage rack and robot module 14 when it is placed within the freezer compartment 24. As is known in the art, it is recommended that the module 14 be placed on an ⅛ inch stainless steel plate 58 in order to distribute load within the compartment 24. The plate 58 includes brackets 60 that are used to secure the stainless steel plate 58 in place on the floor in the freezer compartment 24. Similarly, the frame 50 includes brackets 62 that are screwed into the sidewalls of the freezer compartment 24. The brackets 60, 62 serve to stabilize the module 14 within the freezer compartment 24. Note that standard freezers are typically lined with a stainless steel sheet to which the brackets 60, 62 can be easily attached using screws. The frame 50, the support plates 52, 54, as well as the support columns for the racks 46, and the components of the robot 48 are made of stainless steel. Therefore, material shrinkage due to the ultra-low temperatures within the storage compartment is relatively consistent throughout, and there is little or no need to compensate for thermal distortions after the module 14 has been placed and mounted into the freezer compartment 24 and the system has been cooled.

Figure 4:
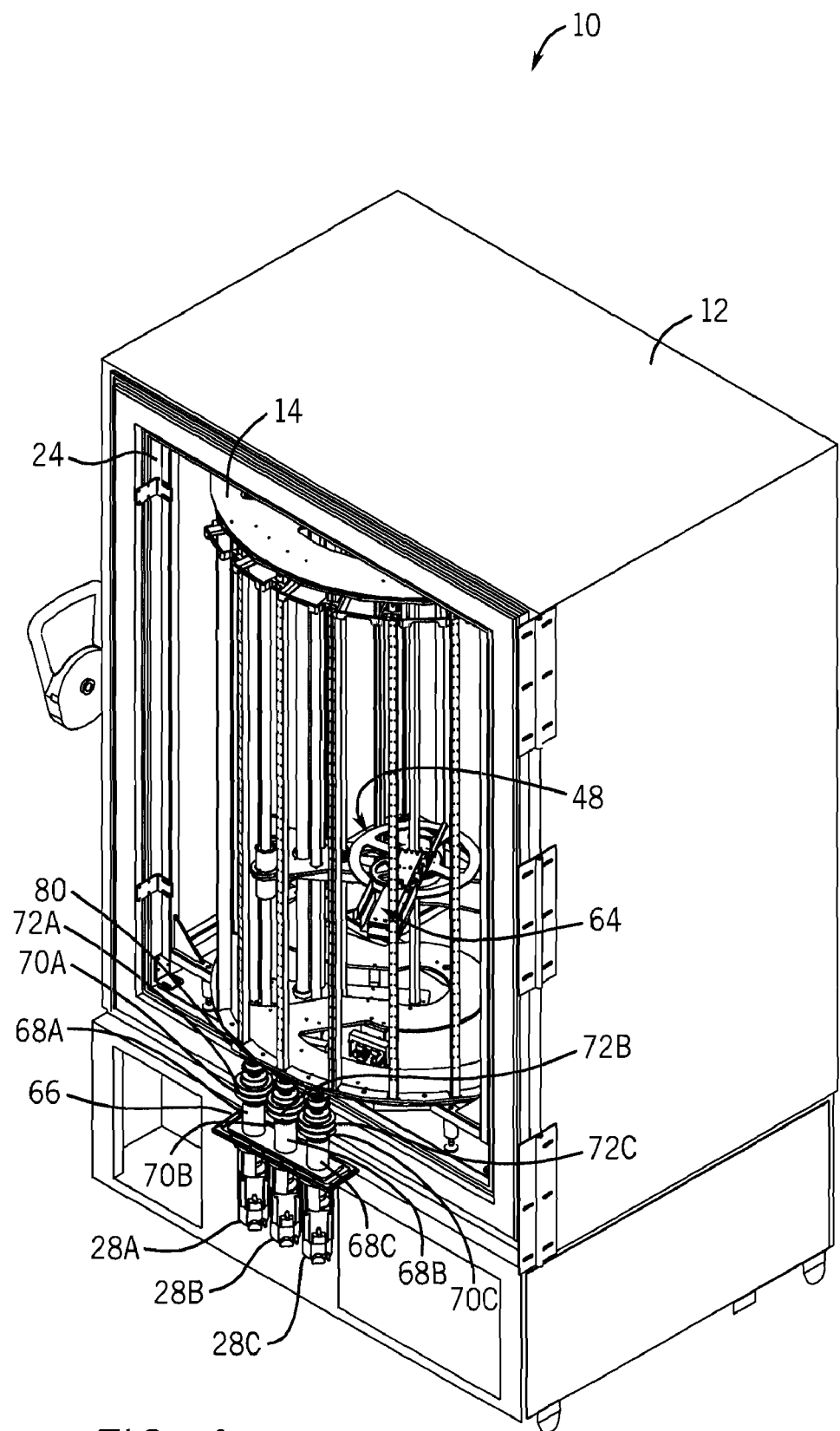
FIG. 4 is a perspective view showing the system of FIG. 1 without the custom, insulated door mounted to the freezer body, and the storage racks and robot being mounted within the storage compartment of the freezer body.

FIG. 4 shows the storage rack and robot module 14 placed and mounted within the freezer compartment 24. In FIG. 4, the insulated door 16 has been removed to show the module 14 inside the freezer compartment 24, although some components that are attached to the door 16 are shown for illustrative purposes. More specifically, three servo motors 28A, 28B and 28C for driving the robot are mounted to or within the custom insulated door 17. The servo motors 28A, 28B and 28C are controlled by the electronic control system in response to requests from the user to place sample storage containers within the system or retrieve samples from the system 10. The preferred servo motor is a brushless AC servo motor, for example, a NEMA rated servo motor having a rated torque of 11.2 inch lbs., rated power of 400 watts and a rated speed of 3,000 rpm. Alternatively, suitable stepper motors can be used. In FIG. 4, servo motor 28A controls vertical motion of the robot reach arm 64, servo motor 28B controls the rotational motion of the reach arm 64, and servo motor 28C controls the motion of the reach arm 64 in the reach direction. The servo motors 28A, 28B and 28C are mounted to a panel 66 on the door 17. The panel 66 shown in FIG. 4 is actually a part of the insulated door 17. The mounting shafts for the servo motor are mounted to plastic, thermal-resistant shafts 68A, 68B and 68C. The thermal-resistant shafts 68A, 68B, 68C pass through insulation within the insulated door panel 17 (not shown in FIG. 4). One set of magnetic couplings 70A, 70B, 70C are attached to the distal end of the thermal-resistant shafts 68A, 68B and 68C. The couplings 70A, 70B, 70C are located within the insulated door 17, below a horizontal panel 72 on the inside surface of the insulated door 17, see FIG. 9. The panel 72 is not shown in FIGS. 4-5 in order to better show the couplings 70A, 70B, 70C. The horizontal panel 72 is preferably made of a fiberglass/epoxy composite known as G10 composite, which resist heat transfer relatively effectively.

Within the freezer compartment 24, there is located another set of magnetic couplers 72A, 72B, 72C. The preferred magnetic coupling is the model MTD-2 from Magnetic Technologies, although other types of magnetic couplings may be used, such as those that are sometimes used in cryogenic applications. Use of the magnetic couplings, as described above, allows transmission of mechanical power from the servo motors 28A, 28B, 28C, which reside outside of the ultra-low temperature freezer compartment 24, through the thermal-resistant panel 72 into the freezer compartment 24 to drive the robot 48.

Figure 5:
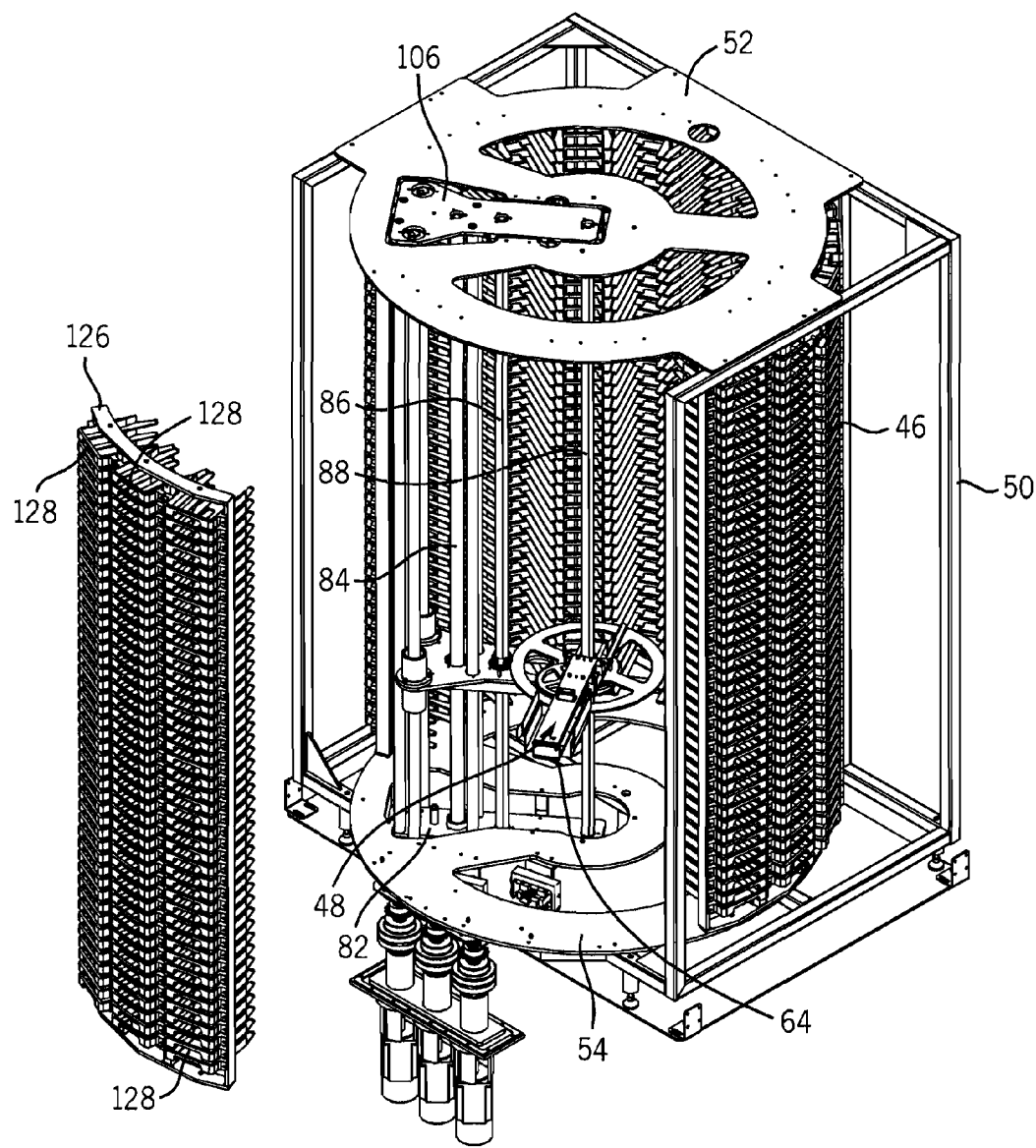
FIG. 5 is a perspective view of the internal components of the system of FIG. 1 showing the stationary storage racks and robots mounted to the frame.
Figure 6:
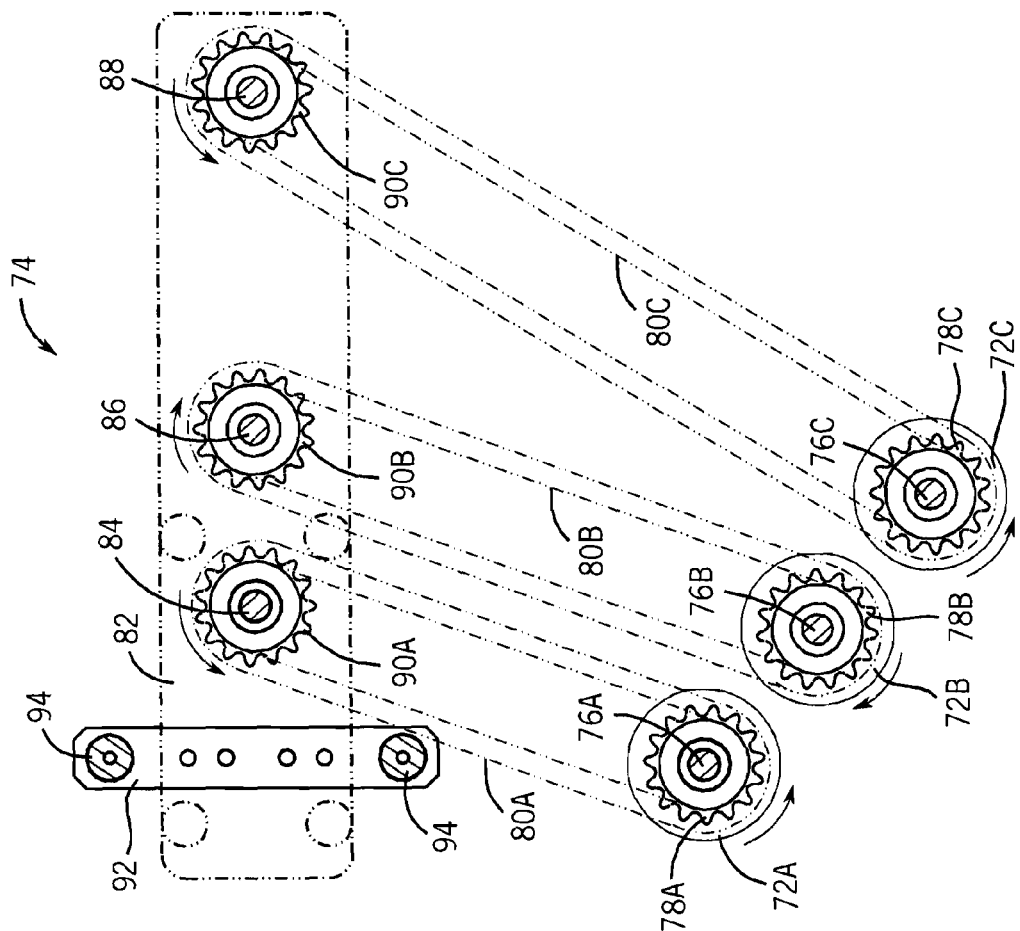
FIG. 6 is a schematic view illustrating chain drives for the robot which are used in accordance with the embodiment of the invention shown in FIG. 1.

Referring to FIG. 6, the preferred robot drive mechanism 74 is a roller chain drive system. Each coupling 72A, 72B, 72C has a shaft 76A, 76B, 76C to which a sprocket 78A, 78B, 78C is attached. The shafts 76A, 76B, 76C are attached at their upper end to a bracket 80 mounted to the frame 50, preferably using unlubricated bearings, although it may be desirable to use dry film lubrication, see e.g. FIG. 4. Still referring to FIG. 6, a stainless steel roller chain 80A, 80B, 80C is associated with each sprocket 78A, 78B, 78C. The sprockets 78A, 78B, 78C are preferably made of stainless steel and designed to match an ANSI size 35 roller chain. The robot base plate 82 is shown at the top of FIG. 6 in phantom. The robot base plate 82 is mounted indirectly to the frame 50 and its lower support plate 54, although it is difficult to see the mounting attachment in the drawings. The vertical lead screw 84 is mounted with a bearing to the base plate 82, as is rotary control bar 86 and reach arm extension bar 88. Bars 86 and 88 preferably have a square cross-section, as depicted in FIG. 5.

Sprockets 90A, 90B, 90C are attached to the lead screw 84, and bars 86, 88, respectively. A bracket 92 is also mounted to the robot base plate 82. The bracket 92 provides a mount for linear guide rails 94.

While the robot drive mechanism shown in FIG. 6 uses roller chains, it may be desirable to use other types of drive systems, for example, stainless steel timing belts, or a gear train using intermediate idler gears. In addition, it may be desirable in some situations to replace the two sets of magnetic couplings 70A, 70B, 70C and 72A, 72B and 72C with a mechanical drive shaft penetrating from the door 17 into the freezer compartment 24, perhaps having bevel gears mating with suitable gears for driving the lead screw 84 and the bars 86, 88. Such a configuration would be less desirable than the use of magnetic couplings, although it is likely to be suitable from the standpoint of heat and moisture ingress into the freezer compartment, as long as suitable seals, such as rotary lip seals, are used around the rotating shafts penetrating into the freezer compartment 24.

Figure 7:
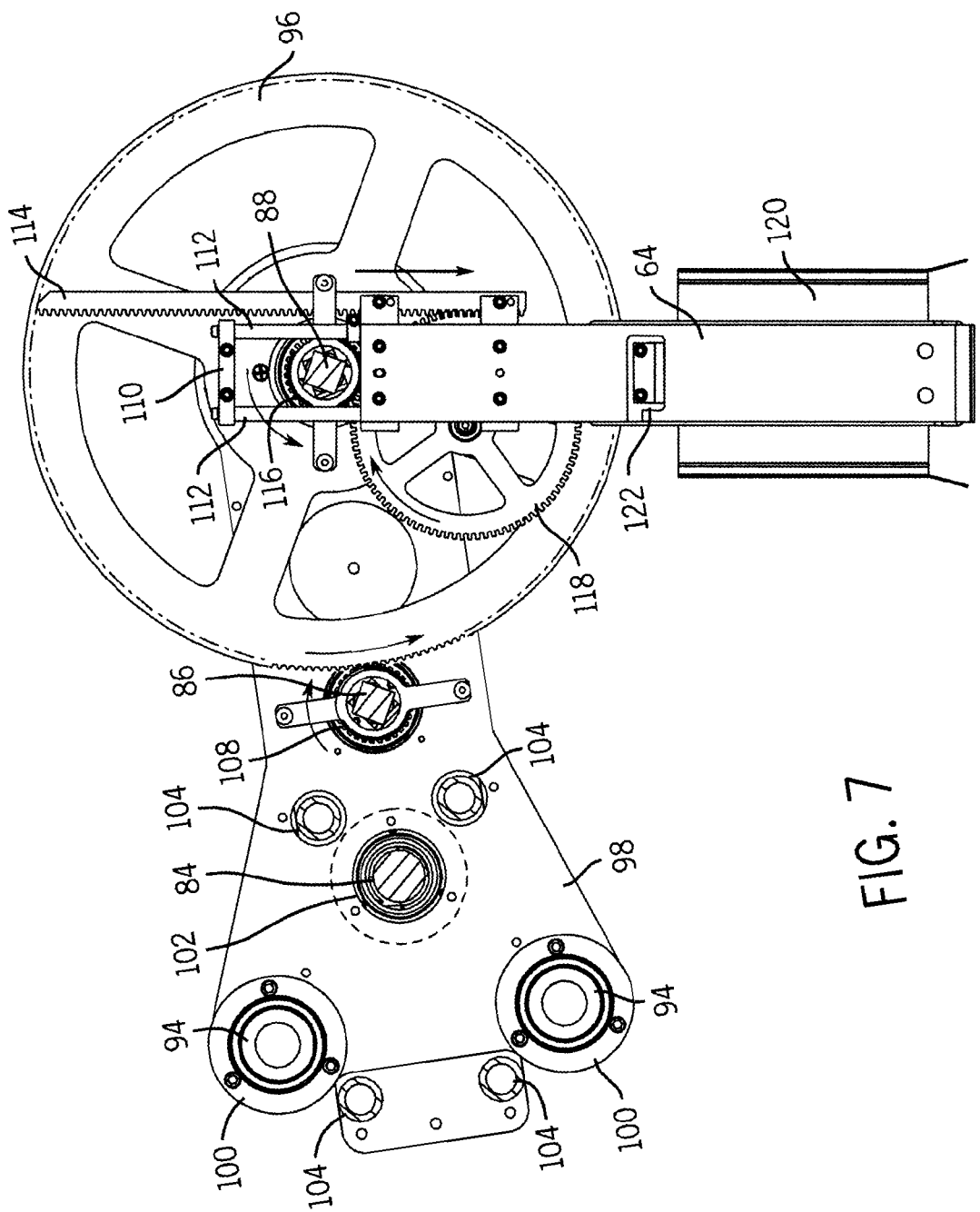
FIG. 7 is a sectional view looking down on components of the robot.

FIG. 7 shows a top view of the robot reach arm 64 as it is mounted on a turntable 96 in accordance with the invention. A reach arm support plate 98 is mounted on vertical guide shafts 94 using bearings 100. The vertical lead screw 84 passes through a threaded opening in, or a threaded coupling 102 attached to, the support plate 98. The support plate 98 as well as the reach arm 94 are raised and lowered by turning the vertical lead screw 84. The support plate 98 includes openings for vertical support rods 104. The support rods 104 span between the lower base plate 82 and the upper plate for the robot 106, FIG. 5. A rotary drive gear 108 is connected to the rotary drive shaft 86. The teeth on the rotary drive gear 108 mesh with teeth on the turntable 96. When the rotary shaft 86 rotates, the turntable 96 in turn rotates.

The reach arm 64 is mounted to the turntable 96, and rotates when turntable 96 rotates. The reach arm 64 includes a slide mechanism that enables the reach arm 64 to extend and retract. The base of the reach arm mechanism 110 is affixed to the turntable 96. Reach arm guide rods 112 extend from the base 110, and the main reach arm platform 64 is slidably mounted over the rods 112, preferably using unlubricated bearings, although it may be desirable to use dry film lubrication for this purpose. A linear rack 114 with teeth is attached to the reach arm platform 64. A gear 116 is mounted to the reach arm extension bar 88, and the teeth of the gear 116 mesh with the teeth on an idler gear 118. The teeth on the idler gear 118 also mesh with the teeth on the linear rack 114 attached to the reach arm platform 64. Thus, the reach arm 64 extends or retracts in accordance with the rotation of shaft 88. Note also that when the turntable 96 rotates counter-clockwise, it causes the reach arm 64 to retract. This retraction is compensated for by the control system.

The reach arm preferably includes a tray 120 with sidewalls, as well as a rear stop 122 and a front lip 124. The dimensions between the stop 122 and the lip 124, as well as the sidewalls of the tray 120, are preferably chosen to capture the standard footprint dimensions for microplates according to the SBS standards, i.e., 3.3654 by 5.0299 inches.

The top end of vertical lead screw 84 and bars 86, 88 are preferably mounted to the top plate 106 using bearings to allow for rotation, whereas the other shafts 94, 104 are mounted to the plates 106, 82 in a fixed manner. It should normally be suitable to use unlubricated bearings, although it may be desirable to use dry film lubricants. Wet lubricants are not recommended for the −80° C. environment.

As mentioned above, it is important that the rotational motion of the turntable and reach arm be accurate. In order to minimize mechanical backlash and improve positional accuracy, it is preferred that the turntable 96 always be rotated in the same direction just prior to the placement or retrieval of a sample storage container in the storage rack. Preferably, the turntable 96 is always rotated in the clockwise direction just prior to placement or retrieval. If robotic movement requires counter-clockwise rotation, the system preferably overshoots in the counter-clockwise direction and then returns in a clockwise direction just prior to placement or retrieval.

Referring to FIG. 5, the storage racks 46 are grouped together, preferably in groups 126 of three vertical columns 128. The groups 126 are attached to the upper support plate 52 and the lower support plate 54 mounted to the frame 50, preferably using screws. The storage racks 46, when mounted, circumvent the robot 48 and reach arm 64 except for the region in which the turntable support plate 98, the vertical lead screw 84 and the vertical guide rods 94 are located. As is known in the art, the structure for the storage racks 46 allows the trays to be set at various heights in order to accommodate sample storage containers having different heights.

Figure 8:
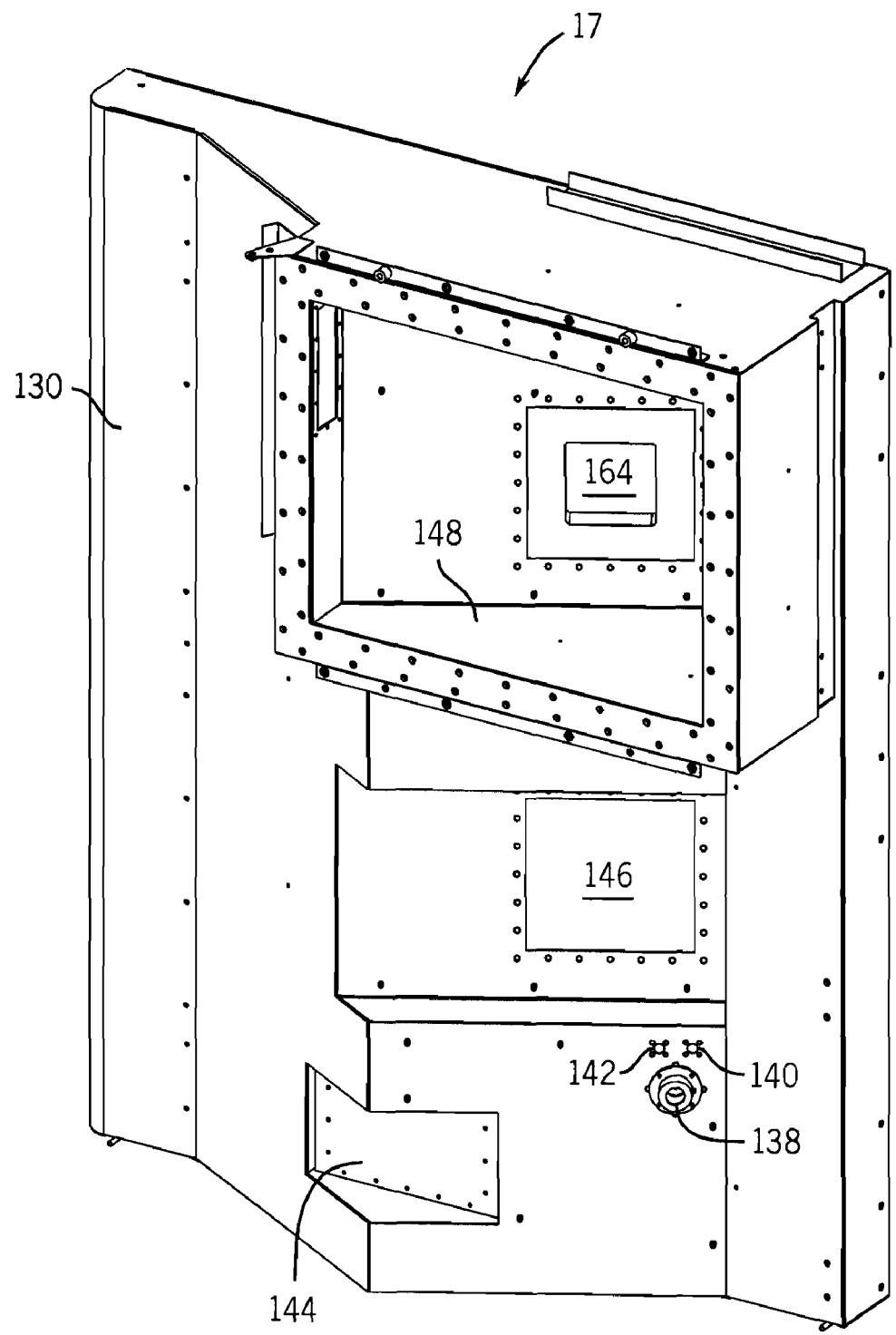
FIG. 8 is a front perspective view of the insulated freezer door, having various components removed.
Figure 9:
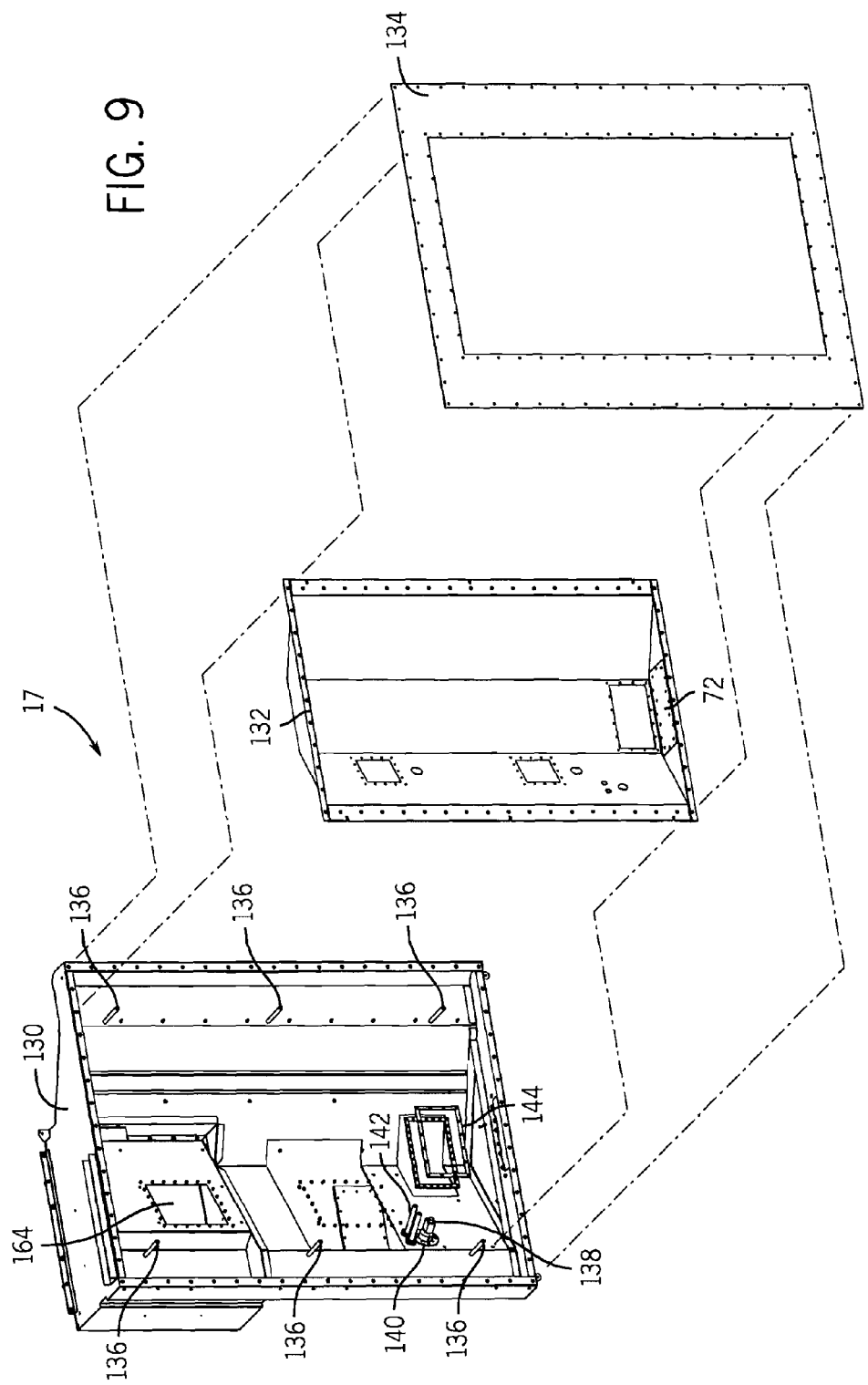
FIG. 9 is an exploded view illustrating the preferred construction of the insulated freezer door.

Referring now to FIGS. 8 and 9, the panel 17 for the custom insulated door includes an outer shell 130, an inner shell 132, and a thermal-resistant panel 134. The outer shell 130 includes standoffs 136 for stabilizing the position of the inner shell 132 when it is attached to the outer shell 130. Although not shown in the drawings, the fully constructed door panel 117 has closed cell polyurethane foam insulation injected between the outer shell 130 and the inner shell 132. The preferred insulation is an R value of 6 to 8 per inch. The thermal-resistant panel 132 is preferably made of the above-mentioned G10 material, which is a thermal-resistant fiberglass/epoxy composite. The thermal-resistant panel 134 is preferably mounted to the inner sleeve 132 with a gasket therebetween, although the gasket is not shown in the drawings.

A vacuum relief valve 138 is mounted to the door panel 17 and is exposed through an opening in the inner sleeve 132 to the ultra-low temperature freezer compartment 24 inside the freezer body 12. The door panel 17 includes a dry gas inlet port 140 which provides access for dry gas into the ultra-low temperature freezer compartment 24. Dry gases bled into the system through port 140 is controlled by the solenoid valve control system 26 shown in FIG. 2. The door panel 17 also includes an outlet port which provides access from the ultra-low temperature freezer compartment 24 to the outside of the system via a controlled solenoid valve system, see FIG. 2, reference number 26. Vacuum relief valves 138 are standard in the art for ultra-low temperature freezer systems. In standard systems, the purpose of the vacuum relief valve 138 is to equalize pressure upon the initial cool down from room temperature to −80° C., or when the door is opened. Failure to provide pressure relief can make it difficult to open the door and can also damage the materials inside of the freezer because of significant pressure drops when cooling to ultra-low temperatures. In the present system, the vacuum relief valve 138 is provided as an emergency override in case there is a substantial negative pressure within the freezer compartment 24. Under normal practice, however, the system 10 will equalize pressure in the freezer compartment 24 by bleeding as necessary dry gas through the dry gas inlet 140 into the freezer compartment 24, or leaking air from the freezer compartment 24 through the outlet 142. In this regard, a pressure sensor (not shown) monitors the pressure at the outlet 142 upstream of the solenoid valve which controls flow through the outlet 142. Preferably, dry gas is bled into the freezer compartment 24 or released to the atmosphere to maintain the pressure within the freezer compartment 24 at or near atmospheric pressure. For example, during the initial cool down, the freezer compartment 24 must cool from room temperature to about −80° C. During this time, air will be bled into the system at a relatively high rate to maintain pressure within the freezer compartment 24, which also serves well to reduce the relative humidity within the freezer compartment 24. Once the system 10 has been initially cooled, the refrigeration compressor will cycle on and off in order to maintain the temperature at about −80° C. The temperature within the ultra-low temperature freezer compartment is therefore likely to cycle between about −82° C./−83° C. to −77° C./−78° C. on a recurring basis. With this change in temperature, the pressure inside the freezer compartment 24 would normally fluctuate if not controlled. When negative pressure occurs within the freezer compartment 24, air and moisture are more likely to leak into the freezer compartment 24 or penetrate through seals into the freezer compartment 24. By using a controlled dry gas bleed (e.g. 3 cubic feet per hour) into the freezer compartment 24, leaks and ingress of air and moisture into the freezer compartment 24 can be reduced. Moreover, supplying dry gas into the freezer compartment 24 when the temperature is relatively low and allowing some air to leak from the system when the temperature is relatively high on a repeated basis helps to reduce the humidity and frost within the freezer compartment 24.

Still referring to FIGS. 8 and 9, the insulated door panel 17 includes a service opening 144 which is normally closed and filled with an insulated plug (not shown). The service opening 144 provides access through the door 17 into the freezer storage compartment 24 for servicing the robot, normally prior to the initial cool down for the system. The door 17 shown in FIGS. 8 and 9 also has an opening 146 for the access module 22, and a chamber 148 for the tube picker 32.

Referring now to FIGS. 10-13, the access module 22 includes a movable tray 150 on which a sample storage container 152 is placed for transfer into the ultra-low temperature storage compartment 24, or for retrieval from the storage compartment 24. The access module 22 includes a door 154 that is opened and closed using a pneumatically controlled mechanism or the like to provide access into and from the freezer compartment 24. Movement of the polycarbonate cover 156 as well as the tray 150 is preferably controlled by stepper motor, for example, NEMA size 17 stepper motors. The access module 22 also includes a polycarbonate cover 156 that covers the tray 150 on which the microplate or tube storage plate 152 is placed. The chamber within the access module 22 is typically at room temperature even when the polycarbonate cover 156 is closed. The mechanical system for moving the tray 150 from the access module 22 into the freezer storage compartment 24 and for opening and closing the door 154 similar to that used in prior systems. Also, it is known in the art to equip the access module 22 with a two-dimensional bar code reader for reading bar codes on the bottom of the storage tubes in containers 150 entering or being retrieved from the system, as well as one-dimensional bar code readers reading bar codes on the containers 150 entering or being retrieved from the system. Bar code information is used to manage plate and tube locations within the storage compartment 24.

Figure 11:
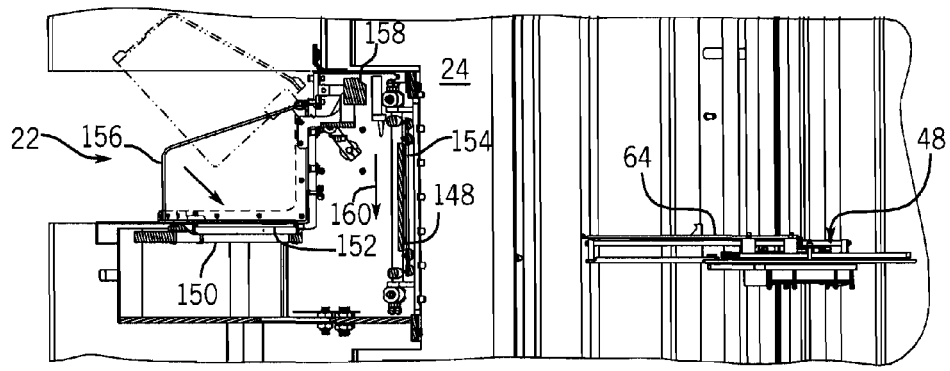
FIGS. 11-13 illustrate the operation of the access module robot reach arm and dry air knife in accordance with one aspect of the invention.
Figure 12:
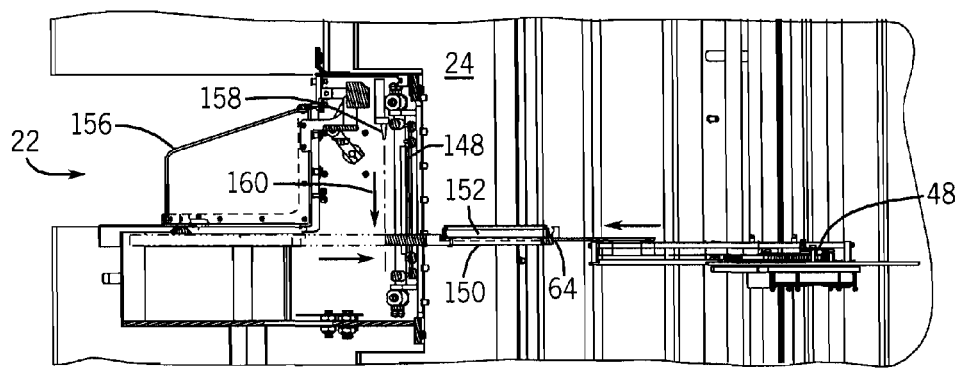
Figure 13:
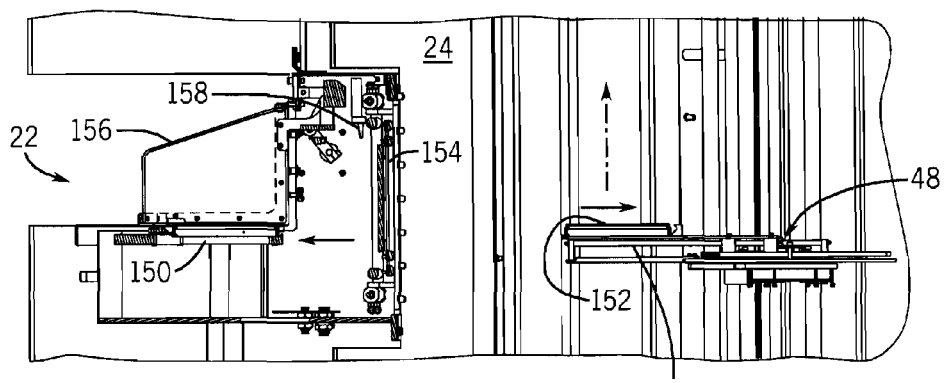

In accordance with one aspect of the invention, dry gas is supplied to an air knife 158, FIGS. 11-13. The air knife 158 is mounted within the access module 32 chamber along a top edge of the opening 146 into the freezer compartment 24, which the door 154 covers. Commercially available aluminum air knives are suitable for this application, for example, the 82000 SlimLine aluminum air knife manufactured by AiRTX International Company. The flow of dry gas, dry air or nitrogen, through the air knife 158 is controlled by a computer controlled solenoid valve. One purpose of the dry gas knife 158 is to reduce moisture within the access module 22 when the polycarbonate cover 156 is closed and the system is ready to either place a sample storage container 152 into the freezer compartment 24 or retrieve a container 152 from the freezer compartment 24. FIGS. 11, 12 and 13 illustrate the process of placing a sample storage container 152 into the freezer compartment 24 in accordance with this aspect of the invention. Referring first to FIG. 11, the sample container 152 is placed on the slidable tray 150 for the access module 22, and the cover 156 is closed. Preferably, the cover 156 does not form an airtight seal when it is closed. Once the cover 156 is closed and the system 10 is instructed to place the sample container 152 in a storage rack 46 within the freezer compartment 24, the control system will begin supplying dry gas to the air knife 158. The air knife 158 outputs a curtain of dry gas into the chamber within the access module 22 and passes in front of the closed door 154. Preferably, a humidity sensor is located within the chamber for the access module 22. The preferred humidity sensor is a Honeywell HIH-4000 series humidity sensor. Also preferably, the door 154 into the freezer compartment 24 will remain shut and the air knife will continue to blow a curtain of dry air 160 into the chamber for the access module 22 until the relative humidity is about 5%-10% within the chamber. This would normally take about thirty seconds under normal operating conditions. Alternatively, instead of using a humidity sensor, the system can operate on a time basis under which the amount of time for blowing dry gas into the closed chamber for the access module 22 would be estimated so that the humidity within the chamber is preferably about 5%-10% RH.

Once the desired relative humidity of 5%-10% has been achieved within the access module chamber 22, the door 154 is open, as illustrated in FIG. 12. The curtain of dry air 160 continues to blow over the opening 148 after the door 154 has been opened. As mentioned, it has been found that the natural convection through the opening 148 upon opening the door 154 is that cold air rushes out of the freezer compartment 24 along the bottom portion of the opening 148 and that warm air rushes into the freezer compartment 24 through the upper portion of the opening 148. Another purpose of the dry air curtain 160 is to disrupt this natural convection. Also, it is believed that some of the dry air in the dry air curtain 160 flows into the ultra-low temperature storage compartment 24, thereby helping to further reduce humidity within the freezer compartment 24. Once the door 154 is opened, the tray 150 for the access module 22 extends into the freezer compartment 24, while at the same time the reach arm 64 for the robot 48 extends in order to transfer the sample storage container 152 from the access module tray 150 to the reach arm 64 for the robot 48. It is preferred that the tray 150 for the access module 22 extends essentially into an empty space with the stationary storage rack 46 within the freezer compartment 24. Upon transfer, the tray 150 is retracted as is the reach arm 64, as shown in FIG. 13. The air knife 158 continues to expel a curtain of dry air 160 until the door 154 is closed.

When a storage plate 152 is retrieved from the system, the sequence of operations described in FIGS. 11, 12 and 13 is quite similar, except that the microplate 152 is transferred from inside of the freezer compartment 24 using the reach arm 64 on the robot 48 to the slidable tray 150 for the access module 22 rather than vice versa. In other words, it is still important in accordance with this aspect of the invention to close the polycarbonate cover 156 for the access module 22, see FIG. 11. Then, operate the air knife 158 to blow a curtain of dry air into the access module 22 to reduce the relative humidity to about 5%-10% within the access module 22 before opening the door 154. Then, continue to blow the dry air curtain from the air knife 154 when the door 154 is opened to pass the sample storage container 152 with the robot reach arm 64 from the freezer compartment 24 onto the slidable tray 150 and into the access module 22. And finally, close the door 154 after the sample storage container 152 has been passed into the access module 22 by tray 150.

Preferably, photoelectric sensors are used to confirm motion external of the freezer compartment 24. For example, it is desirable to use photo detectors to confirm whether the door 154 covering the opening 146 into the freezer compartment 24 is opened or closed, to determine whether the cover 156 for the access module 22 is opened or closed, and to confirm whether the tray 150 is in a fully retracted or fully extended position. Moreover, while not shown in the drawings, it is desirable to provide a vertical series of photo sensors which detect the height of a sample storage container 152 placed in the tray 150 in the access module 22 before transferring the container 152 into the storage racks within the freezer compartment 24. Preferably, each sensor in the vertical series is placed optimally to detect the most common heights for microplates or tube storage racks in the industry. For example, the lowest photo detector preferably senses the presence of a shallow well microplate, but a shallow well microplate would not trigger detectors at heights above the lowest detector (14.35 mm). The second lowest detector preferably detects a half height storage container, a third detector is preferably placed at the height of a full height storage container; the fourth detector preferably at 50 mm; and, the fifth detector preferably at 75 mm. In this manner, the control system can confirm that the sample storage container 152 will fit into the designated location within the storage compartment 24. The height for each storage location is preferably mapped within the computer control system.

Figure 10:
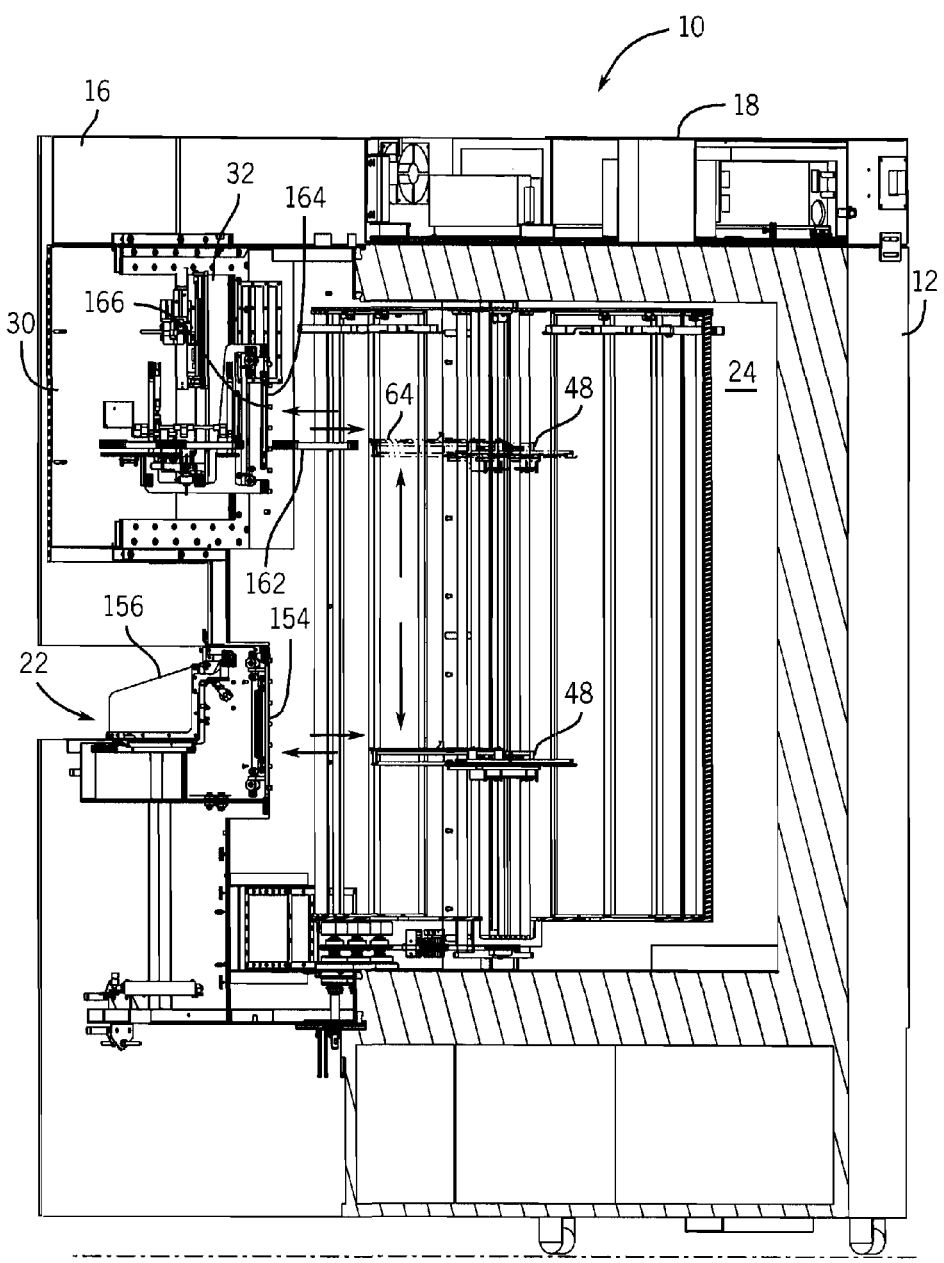
FIG. 10 is a view of the overall system shown in FIG. 1 having parts broken away in order to schematically view the internal components.

Referring again to FIG. 10, the preferred custom insulated door 16 also includes a compartment 30 for holding a tube picking apparatus 32. The robot 48 can be instructed to bring a storage container containing sealed storage tubes of biological or chemical samples to a location within the freezer compartment 24 for transferring the sample storage container to a slidable tray 162 associated with the tube picking apparatus 32 residing in the compartment 30. The tube picking compartment 30 includes an opening 164, FIGS. 8 and 9, for providing access to the tube picking chamber 30 from the freezer compartment 24 and vice versa. An access shutter or door 166, which is controlled by a pneumatically controlled mechanism, opens and closes to provide access. In FIG. 10, the door 166 is in the open position for shuttling plates into and out of the tube picker compartment 30. This invention does not address the operation and construction of the tube picking apparatus itself. One aspect of the invention, however, is directed to controlling the environment within the tube picking chamber 30. In accordance with this aspect of the invention, the tube picking chamber 30 is cooled to a temperature of about −5° C. to −20° C., preferably about −20° C. In this manner, as mentioned, the tube picking mechanism 32 can operate in a less harsh environment, which greatly improves its reliability. Moreover, a dry gas supply port (not shown) provides dry gas into the chamber 30 through an electronically controlled solenoid valve in order to lower the humidity within the chamber 30 to, for example, less than 2% relative humidity, before opening the door 166. A humidity sensor (not shown) is preferably located within the chamber 30 in order to monitor the humidity within the chamber and control the flow of dry gas accordingly. Once the chamber 30 has achieved the desired level of relative humidity, the control system then opens the door 166 to cool the chamber 30 to the desired intermediate cold temperature of about −20° C. A temperature sensor (not shown) is provided within the chamber 30. When the tube picking mechanism 32 is in use, the system will preferably attempt to maintain the −20° C. temperature within the chamber 30 by opening and closing the door or shutter 166 accordingly. This allows a single refrigeration system to support both environments. As mentioned, use of a separate climate-controlled tube picking chamber 30 within the system 10 eliminates the need to retrieve multiple storage containers from the system 10 through the access module 22 when sample tubes from different storage containers are desired to be retrieved from the system 10. This feature therefore not only protects other samples from premature thaw and harm, but also reduces the risk of moisture flow into the ultra-low temperature freezer compartment 24. Moreover, with this configuration, tube storage containers can be shuttled in and out of the tube picking compartment 30 at a relatively fast pace, for example, one or two minutes per storage container. The configuration therefore shortens exposure of samples not selected for retrieval outside of the −80° C. environment.

The invention has been described herein with respect to an ultra-low temperature storage environment, however, many of the features described herein may be useful for conventional freezer storage systems that store samples at freezing temperatures above the ultra-low temperature range. For example, many features of the invention may be applied to conventional freezer systems which maintain the freezer compartment at −20° C.

We claim:

1. An automated storage and retrieval system for storing sample storage containers at ultra-low temperatures, the system comprising:
   a freezer body having an ultra-low temperature, insulated compartment that is maintained at an ultra-low temperature from about −50° C. to −90° C. under normal operating conditions when biological or chemical samples are being stored in the ultra-low temperature compartment;
   at least one storage rack having trays for storing storage containers holding biological or chemical samples;
   a robot located within the ultra-low temperature freezer compartment and also mounted to the frame, the robot having an automatically controlled reach arm for transporting storage sample containers within the freezer compartment;
   an insulated freezer door that is mounted to the freezer body and closed during normal operation of the system;
   an access module on the door for introducing a sample storage container into the ultra-low temperatures freezer compartment and retrieving containers from the ultra-low temperatures freezer compartment through the door when the door is closed, the access module providing a chamber in which moisture is purged before providing access into the ultra-low temperatures freezer compartment;
   robot drive motors mounted to the door outside of the ultra-low temperatures compartment; and
   a transmission that transmits power from the robot drive motors outside of the ultra-low temperatures compartment to the robot inside the ultra-low temperatures compartment.

2. The system as recited in claim 1 wherein at least some of the sample storage containers in the ultra-low temperatures compartment hold sealed tubes containing biological samples and the system further comprises a tube picking compartment on the door that contains a tube picking mechanism and also has an access door to provide access between the tube picking compartment and the ultra-low temperatures storage compartment within the freezer via the robot, the tube picking chamber being maintained at a freezing temperature above the ultra-low temperature maintained in the freezer storage compartment.

3. The system as recited in claim 2 wherein the temperature in the tube picking chamber is maintained in part by bleeding air from the ultra-low temperatures storage compartment into the tube picking chamber.

4. The system as recited in claim 1 wherein the transmission comprises a first set of magnetic couplings mounted to output shafts from the robot drive motors mounted to the door and being located outside of the ultra-low temperatures compartment, and a second set of complimentary magnetic couplings each mounted to a drive for controlling the motion of the robot inside of the ultra-low temperatures compartment, the complimentary magnetic couplings being located within the ultra-low temperatures freezer compartment.

5. The system as recited in claim 1 wherein the transmission comprises mechanical couplings that couple the robot drive motors to the robot drive mechanism inside of the ultra-low temperatures freezer compartment, the mechanical couplings passing through an inner surface of the door and coupling to the robot inside of the ultra-low temperatures compartment.

6. The system as recited in claim 1 wherein the freezer body has a continuous inner wall with no penetration by any mechanical component except for the door.

7. The system as recited in claim 1 wherein the door includes a service opening that provides access to the robot drive mechanism within the ultra-low temperatures freezer compartment, the service opening being normally closed with an insulated plug after system installation when the system is not being serviced.

8. The system as recited in claim 1 wherein the access module further comprises a dry gas knife which blows a curtain of dry gas over the access opening when the access door into the ultra-low temperatures freezer compartment is open.

9. An automated storage and retrieval system for storing sample storage containers at ultra-low temperatures, the system comprising:
a freezer having an ultra-low temperatures compartment that is maintained at an ultra-low temperature from about −50° C. to −90° C. under normal operating conditions when biological or chemical samples are being stored within the insulated ultra-low temperatures compartment;
a storage rack having trays for storing sample storage containers;
a robot located within the insulated ultra-low temperatures freezer compartment having an automatically controlled reach arm for transporting sample storage containers within the freezer compartment, the robot also having mechanical drive components located within the ultra-low temperatures freezer compartment;
an access module for introducing sample storage containers into the ultra-low temperatures freezer compartment and for retrieving containers from the ultra-low temperatures storage compartment, the access module providing a chamber in which moisture is purged before providing access into and from the ultra-low temperatures storage compartment;
robot drive motors mounted outside of the ultra-low temperatures storage compartment; and
magnetic couplings for transmitting power from the robot drive motors outside of the ultra-low temperature compartment to the robot drive mechanism inside the ultra-low temperature compartment.

10. The system as recited in claim 9 wherein the robot drive motors are mounted in a fixed location with respect to the freezer under normal operating conditions.

11. The system as recited in claim 9 wherein the magnetic couplings comprise a first set of magnetic couplings mounted to output shafts from the robot drive motors mounted to the door and being located outside of the ultra-low temperature compartment, and a second set of complimentary magnetic couplings each mounted to a drive for controlling the motion of the robot inside of the ultra-low temperature compartment, the complimentary magnetic couplings being located within the ultra-low temperature freezer compartment.

12. The system as recited in claim 11 wherein the freezer comprises an insulated freezer body and an insulated freezer door that is mounted to the freezer body and is closed during normal operation of the system, and wherein the robot drive motors and the first set of magnetic couplings are mounted to the insulated freezer door outside of the ultra-low temperature compartment.

13. The system as recited in claim 12 wherein the ultra-low temperature freezer compartment contains no penetration of any components to drive the robot.

14. An automated storage and retrieval system for storing sample storage containers at ultra-low temperatures, the system comprising:
a freezer having an insulated, ultra-low temperature compartment that is maintained at an ultra-low temperature from about −50° C. to about −90° C. under normal operating conditions when biological or chemical samples are being stored within the ultra-low temperature compartment; the freezer having an insulated door that closed during the normal operation of the system
a storage rack having trays for storing sample storage containers holding biological samples;
a robot located within the ultra-low temperature freezer compartment, the robot having an automatically controlled reach arm for transporting sample storage containers within the ultra-low temperature freezer compartment; and
an access module for introducing sample storage containers into the ultra-low temperature freezer compartment and for retrieving containers from the ultra-low temperature freezer compartment, the access module providing a chamber in which moisture is purged before providing access into the ultra-low temperature freezer compartment; and
further wherein the robot provides controlled motion for the reach arm along three degrees of freedom comprising substantially vertical movement, substantially horizontal movement and rotational movement, and wherein the robot further comprises a turntable that supports the reach arm and which has a rotational axis parallel to and offset from the vertical lead screw residing along a fixed vertical axis within the ultra-low temperature compartment; robot drive motors mounted to the door outside of the ultra-low temperatures compartment; and a transmission that transmits power from the robot drive motors outside of the ultra-low temperatures compartment to the robot inside the ultra-low temperatures compartment.

15. The system as recited in claim 14 wherein the storage rack comprises a plurality of columns arranged circumferentially about the rotational axis of the turntable except for a portion of the circumference in which the vertical lead screw and a turntable support mechanism reside.

16. The system as recited in claim 14 wherein the storage rack is fixed in a location within the ultra-low temperature freezer compartment and does not rotate therein.

17. The system as recited in claim 14 further comprising a frame located within the insulated ultra-low temperature freezer compartment, wherein the robot is mounted to the frame.

18. The system as recited in claim 15 further comprising upper and lower rack support plates which are mounted to the frame into which the storage racks are mounted.

19. The system as recited in claim 14 wherein the robot comprises a drive mechanism for each of the three degrees of motion, and each drive consists of a chain drive and gears which turn to impart motion for the reach arm.

20. The system as recited in claim 14 wherein the turntable is able to rotate in a first direction and a second direction and the system further comprises control means for operating the robot in order to place or retrieve the sample storage container from the tray in the storage rack such that the turntable is rotated in the first direction prior to placing a retrieval in order to minimize positional inaccuracies due to mechanical backlash.

21. An automated storage and retrieval system for storing sample storage containers at ultra-low temperatures, the system comprising:

a freezer having an insulated, ultra-low temperature compartment that is maintained at an ultra-low temperature from about −50° C. to about −90° C. under normal operating conditions when biological or chemical samples are being stored within the ultra-low temperature compartment; the freezer having an insulated door that closed during the normal operation of the system a storage rack having trays for storing sample storage containers holding biological samples;

a robot located within the ultra-low temperature freezer compartment, the robot having an automatically controlled reach arm for transporting sample storage containers within the ultra-low temperature freezer compartment; and an access module for introducing sample storage containers into the ultra-low temperature freezer compartment and for retrieving containers from the ultra-low temperature freezer compartment, the access module providing a chamber in which moisture is purged before providing access into the ultra-low temperature freezer compartment;

a pressure sensor for monitoring the pressure within the ultra-low temperature freezer compartment;

a source of dry gas; and a dry gas inlet port through which dry gas can be supplied from the source of dry gas into the ultra-low temperature freezer compartment; robot drive motors mounted to the door outside of the ultra-low temperatures compartment; and a transmission that transmits power from the robot drive motors outside of the ultra-low temperatures compartment to the robot inside the ultra-low temperatures compartment.

22. The automated storage and retrieval system as recited in claim 21 further comprising an electronically controlled valve for controlling the flow of dry gas through the dry gas inlet into the ultra-low temperature freezer compartment.

23. The automated storage and retrieval system as recited in claim 21 further comprising an outlet port having an electronically controlled valve for allowing air to exit the ultra-low temperature freezer compartment on a controlled basis.

* * * * *